(12) United States Patent
Beuther et al.

(10) Patent No.: US 8,491,741 B2
(45) Date of Patent: Jul. 23, 2013

(54) METHOD OF FORMING ELASTOMERIC LAMINATES HAVING TARGETED ELASTIC PROPERTIES FOR USE IN PERSONAL CARE ARTICLES

(75) Inventors: Paul D. Beuther, Neenah, WI (US); Brian K. Rhodes, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 393 days.

(21) Appl. No.: 12/981,167

(22) Filed: Dec. 29, 2010

(65) Prior Publication Data

US 2012/0168063 A1 Jul. 5, 2012

(51) Int. Cl.
*B32B 37/00* (2006.01)

(52) U.S. Cl.
USPC ............................ 156/163; 156/164; 156/229

(58) Field of Classification Search
USPC .................................. 156/160, 163, 164, 229
See application file for complete search history.

(56) References Cited

U.S. PATENT DOCUMENTS

| | | | |
|---|---|---|---|
| 5,422,172 A | 6/1995 | Wu | |
| 5,660,657 A | 8/1997 | Rajala et al. | |
| 5,861,074 A | 1/1999 | Wu | |
| 6,069,097 A | 5/2000 | Suzuki et al. | |
| 6,255,236 B1 * | 7/2001 | Cree et al. | 442/328 |
| 6,521,320 B2 | 2/2003 | McCabe et al. | |
| 6,830,800 B2 | 12/2004 | Curro et al. | |
| 7,037,569 B2 | 5/2006 | Curro et al. | |
| 7,083,691 B2 * | 8/2006 | Hamulski et al. | 156/73.1 |
| 7,320,948 B2 | 1/2008 | Morman et al. | |
| 7,470,340 B2 * | 12/2008 | Baldauf et al. | 156/73.1 |
| 7,585,382 B2 | 9/2009 | Hughes et al. | |
| 7,601,657 B2 | 10/2009 | Zhou et al. | |
| 7,651,653 B2 | 1/2010 | Morman et al. | |
| 7,674,733 B2 | 3/2010 | Wu et al. | |
| 2004/0108043 A1 | 6/2004 | Otsubo | |
| 2004/0127876 A1 | 7/2004 | Stevens | |
| 2006/0148361 A1 | 7/2006 | Ng et al. | |
| 2006/0246803 A1 | 11/2006 | Smith et al. | |
| 2007/0048497 A1 | 3/2007 | Zhou et al. | |
| 2007/0254547 A1 | 11/2007 | Ducauchuis et al. | |
| 2007/0287348 A1 | 12/2007 | Autran et al. | |
| 2008/0076315 A1 | 3/2008 | McCormack et al. | |
| 2008/0095978 A1 | 4/2008 | Siqueira et al. | |
| 2008/0311338 A1 | 12/2008 | Petersen et al. | |

(Continued)

FOREIGN PATENT DOCUMENTS

| | | |
|---|---|---|
| WO | WO 00/46023 A2 | 8/2000 |
| WO | WO 01/54900 A1 | 8/2001 |
| WO | WO 2010/050867 A1 | 5/2010 |

*Primary Examiner* — Jeff Aftergut
(74) *Attorney, Agent, or Firm* — Henry Michael Kubicki

(57) ABSTRACT

A method of forming an elastomeric laminate having targeted elastic properties for use in personal care articles is disclosed. In particular embodiments, the method comprises providing first and second nonwoven webs; providing a core layer of elastomeric material under tension; sandwiching the core layer between the first and second nonwoven webs; bonding the core layer to at least one of the first and second nonwoven webs; providing an elastomeric film ribbon web under tension; sandwiching the elastomeric film ribbon web between the first and second nonwoven webs; and fusing the elastomeric film ribbon web to the first and second nonwoven webs. In particular embodiments, the core layer of elastomeric material is an elastomeric film web core layer. In particular embodiments, the elastomeric film ribbon web, the core layer, or both is/are bonded to the first and second nonwoven webs solely by fusing, without the use of adhesive.

18 Claims, 6 Drawing Sheets

U.S. PATENT DOCUMENTS

2009/0038751 A1 2/2009 Hermansson et al.
2009/0197041 A1 8/2009 Lake et al.
2010/0059168 A1 3/2010 Endo et al.
2010/0298798 A1 11/2010 Lakso et al.
2011/0094661 A1 4/2011 Thorson
2011/0098668 A1 4/2011 Thorson et al.

* cited by examiner

METHOD OF FORMING ELASTOMERIC LAMINATES HAVING TARGETED ELASTIC PROPERTIES FOR USE IN PERSONAL CARE ARTICLES

BACKGROUND

Disposable personal care articles are common in society, including diapers, training pants, enuresis pants, adult incontinence garments, feminine hygiene articles, surgical garments, protective wear, and the like. Frequently, such articles are constructed of polymeric substrates, including, for example, polyolefin films and polyolefin nonwovens like spunbond materials or carded web materials. It is commonly desirable to provide such articles with elastic properties, such as via the use of elastic strands or elastic films. It is also commonly desirable to provide such articles with targeted or localized elastic properties for specific functionality. For example, it is frequently desirable to provide elasticization at one of more edges of certain articles, such as at the leg and waist opening of garments, at the crotch edge of menstrual or incontinence pads, or at the wrist or neck openings of disposable garments, such as surgical or safety gowns or coats. The conventional approach to providing such elasticization has been to adhesively fix rubber-like strands of elastomeric material to the polymeric substrate. Upon release of the tensioning force, the elastic strands gather the substrate, providing the desired functional properties, such as, for example, providing a snug fit around the leg or waist opening of a disposable garment. This conventional approach to elasticization requires the use of adhesive to bond the elastic strands to the substrate, and to hold them in place when under tension. Such adhesive adds cost and process complexity to the manufacture of such articles. In addition, there is restricted ability to recycle waste and scrap from such a manufacturing process because such waste or scrap contains a mix of components—polyolefin substrates, rubber-like elastic threads, and adhesive. Therefore, what is needed is an improved method of providing targeted or localized elastic properties in disposable personal care articles without the need for adhesive.

SUMMARY OF PARTICULAR EMBODIMENTS OF THE INVENTION

In one aspect, the present invention relates to a method of forming an elastomeric laminate having targeted elastic properties for use in personal care articles. The method defines a machine direction and a cross-machine direction. In particular embodiments, the method comprises providing first and second nonwoven webs, each defining a cross-direction width; providing a core layer of elastomeric material under tension, the core layer having a cross-direction width at least 75% that of the width of at least one of the first and second nonwoven webs; sandwiching the core layer of elastomeric material between the first and second nonwoven webs; bonding the core layer of elastomeric material to at least one of the first and second nonwoven webs; providing an elastomeric film ribbon web under tension; sandwiching the elastomeric film ribbon web between the first and second nonwoven webs; and bonding the elastomeric film ribbon web to the first and second nonwoven webs by fusing the elastomeric film ribbon web to the first and second nonwoven webs. In particular embodiments, the elastomeric film ribbon web is bonded to the first and second nonwoven webs solely by fusing, without the use of adhesive. In particular embodiments, the core layer of elastomeric material is an elastomeric film web core layer. In particular embodiments, bonding the core layer of elastomeric material to at least one of the first and second nonwoven webs comprises fusing the elastomeric film web core layer to the at least one of the first and second nonwoven webs. In particular embodiments, the elastomeric film web core layer is bonded to at least one of the first and second nonwoven webs solely by fusing, without the use of adhesive.

In another aspect, the present invention relates to a method of manufacturing a personal care garment, the garment comprising an elastomeric laminate having targeted elastic properties. The method defines a machine direction and cross-machine direction. In particular embodiments, the method comprises providing first and second nonwoven webs, each defining a cross-direction width; providing a core layer of elastomeric material under tension, the core layer having a cross-direction width at least 75% that of the width of at least one of the first and second nonwoven webs; sandwiching the core layer of elastomeric material between the first and second nonwoven webs; bonding the core layer of elastomeric material to at least one of the first and second nonwoven webs; providing an elastomeric film ribbon web under tension; sandwiching the elastomeric film ribbon web between the first and second nonwoven webs; and bonding the elastomeric film ribbon web to the first and second nonwoven webs by fusing the elastomeric film ribbon web to the first and second nonwoven webs. In particular embodiments, the personal care garment when donned defines a waist opening and two leg openings, and the elastomeric film ribbon web is positioned adjacent the waist opening, one or both of the two leg openings, or both the waist opening and the leg openings.

Various embodiments of the present invention can in particular instances provide efficient techniques for manufacturing elastomeric laminates for use in constructing personal care articles. In particular embodiments, such techniques eliminate the use of adhesive in the laminating stage of the process, thereby reducing material and potentially capital equipment cost. Furthermore, the ease with which scrap materials may be recycled may, in certain embodiments, be improved.

DEFINITIONS

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least percent of its relaxed length and which will recover, upon release of the applied force, at least 20 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

"Fusing" and its derivatives mean to unite two materials by at least partially thermally melting one or both of them. Two materials will be considered to be fused together when they are fused directly to one another or indirectly to one another, such as when each is directly fused to intermediate materials.

"Integral" is used to refer to various portions of a single unitary element rather than separate structures bonded to or placed with or placed near one another.

"Layer" when used in the singular can have the dual meaning of a single element or a plurality of elements.

These terms may be defined with additional language in the remaining portions of the specification.

DETAILED DESCRIPTION OF EXEMPLARY EMBODIMENTS

Figure 1:
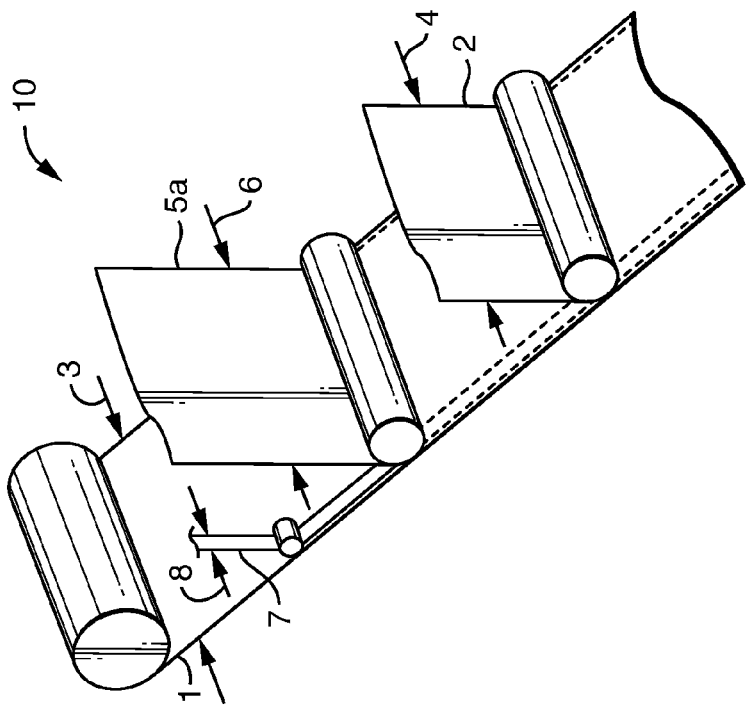
FIG. 1 representatively illustrates a perspective view of one embodiment of an elastomeric laminate manufacturing process incorporating principles of the present invention.
Figure 2:
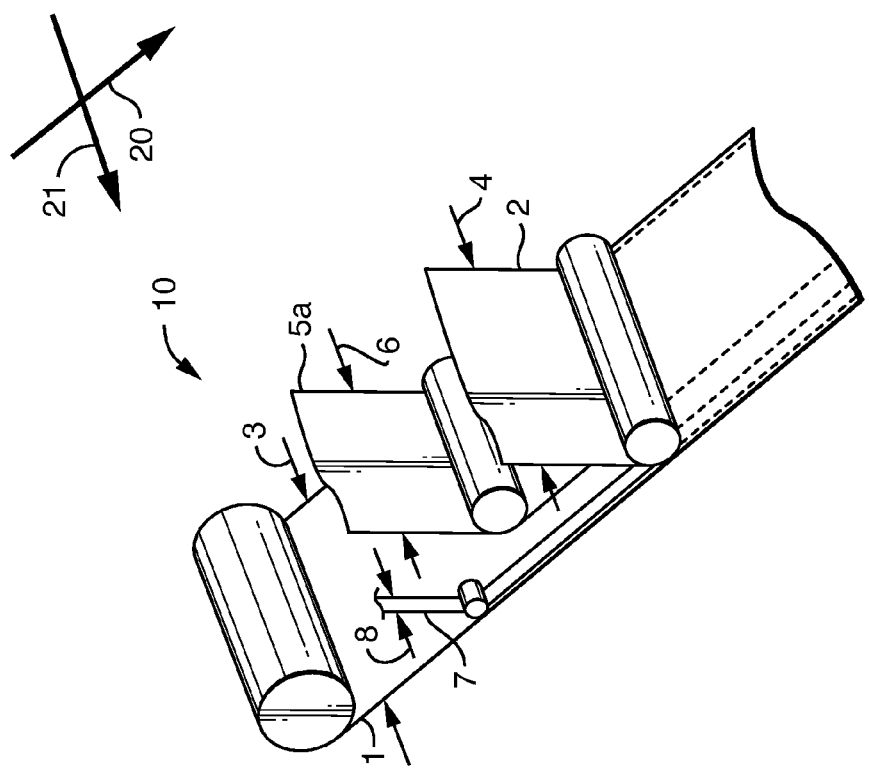
FIG. 2 representatively illustrates a perspective view of an alternative embodiment of an elastomeric laminate manufacturing process incorporating principles of the present invention.
Figure 3:
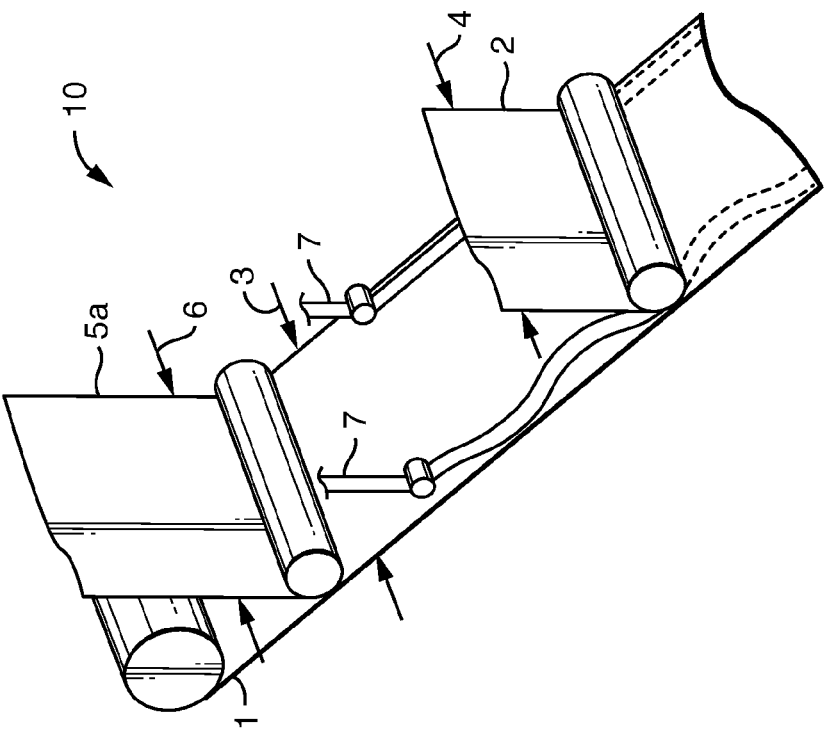
FIG. 3 representatively illustrates a perspective view of another alternative embodiment of an elastomeric laminate manufacturing process incorporating principles of the present invention.
Figure 4:
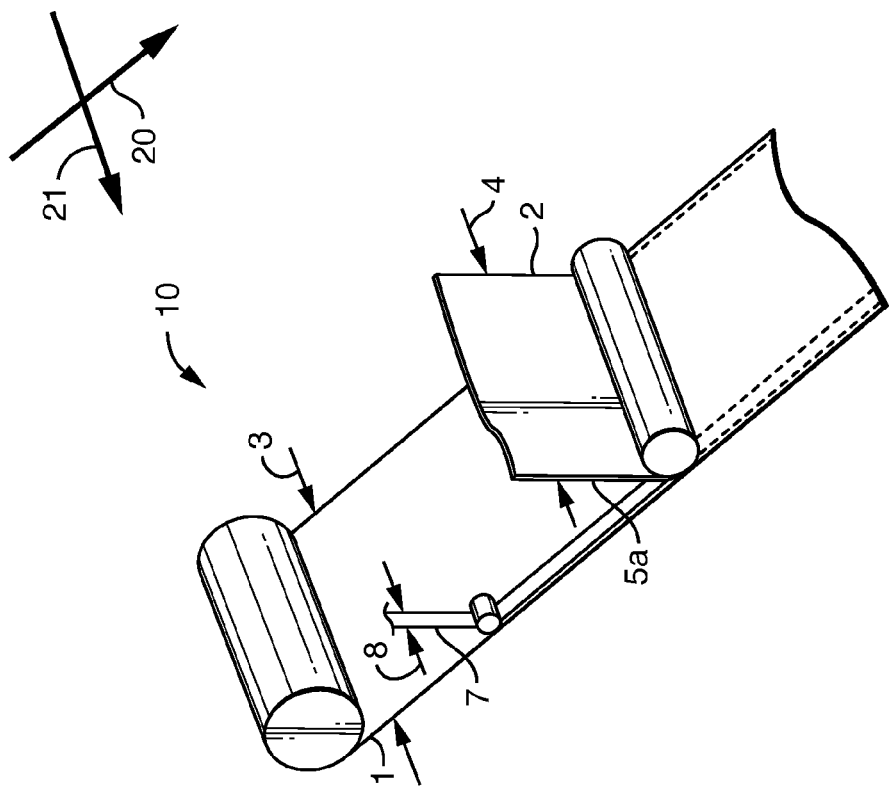
FIG. 4 representatively illustrates a perspective view of yet another alternative embodiment of an elastomeric laminate manufacturing process incorporating principles of the present invention.
Figure 5:
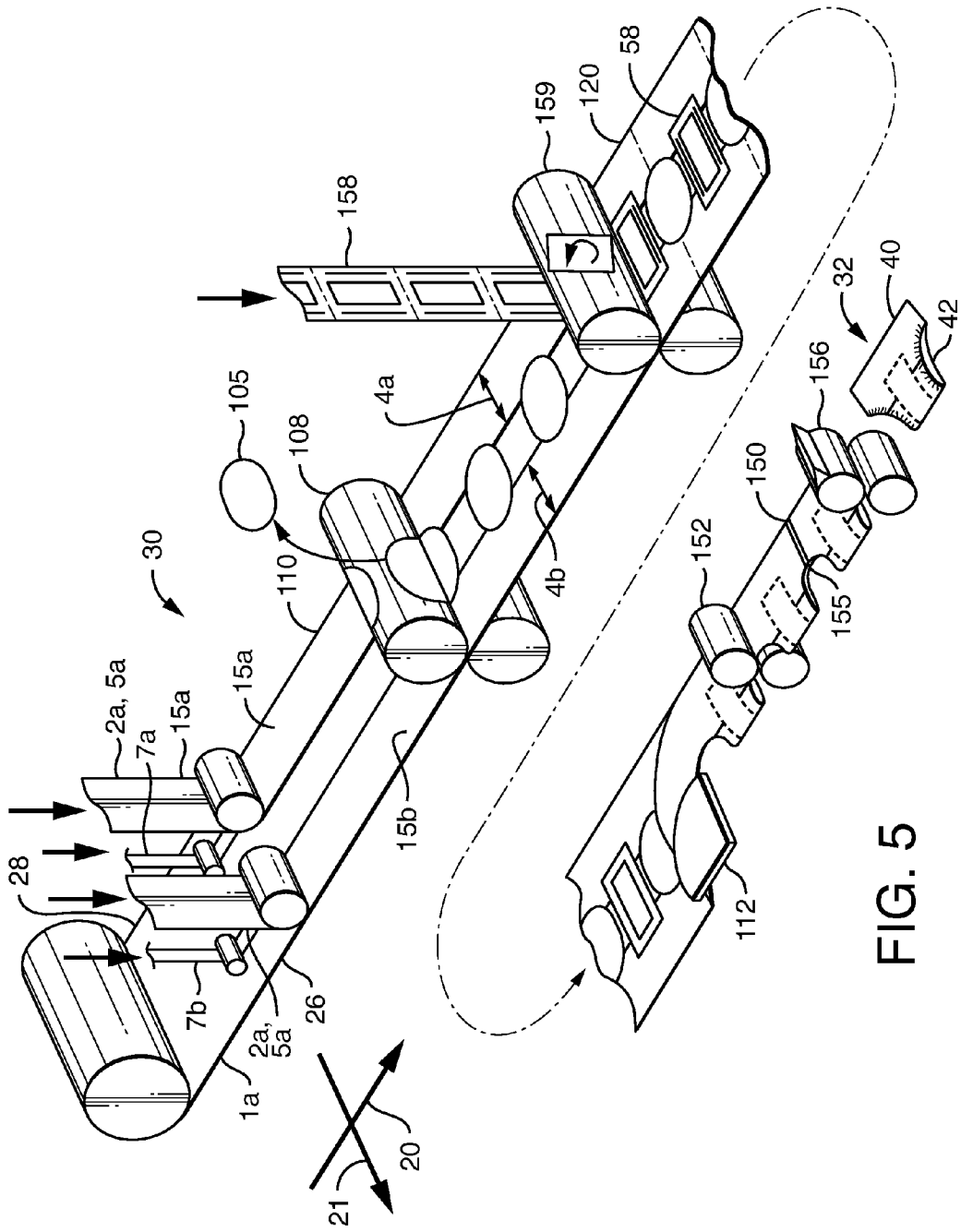
FIG. 5 representatively illustrates a perspective view of one embodiment of a garment manufacturing process incorporating principles of the present invention.

Reference to FIGS. 1-8 shall be made in describing various examples which incorporate certain principles of the invention. It should be noted that the embodiments depicted in FIGS. 1-8 are merely representative examples of the invention. Although for illustrative purposes certain features of the present invention shall be described and illustrated with respect to a "cross-direction" garment manufacturing process, the various aspects and embodiments of the present invention are suitable for use with both "machine-direction" and "cross-machine-direction" processes, and include processes for making such garments as disposable diapers, disposable swim pants, disposable training pants, disposable enuresis garments, feminine care products, surgical garments, and the like.

In one aspect, the present invention pertains to a method of forming an elastomeric laminate having targeted elastic properties for use in personal care articles. Referring to FIGS. 1-4, the method 10 defines a machine direction 20 and a cross-machine direction 21. The method includes providing a first nonwoven web 1 defining a cross-direction width 3, and a second nonwoven web 2 defining a cross-direction width 4. The method further comprises providing a core layer of elastomeric material 5 under tension. The core layer defines a width 6. The core layer could be a series of elastomeric strands; in such a case the width 6 is the distance in the cross-machine direction 21 measured between the outer edges of the two outermost strands. Preferably, the core layer 5 is an elastomeric film web core layer 5a. In particular embodiments, the core layer 5 has a cross-direction width 6 at least 75%, more particularly at least 90%, and still more particularly approximately 100% that of at least one of the width 3 of the first nonwoven web 1 and the width 4 of the second nonwoven web 2.

The method further includes providing an elastomeric film ribbon web 7 under tension. The ribbon web 7 has a cross-direction width 8 suitable to provide the desired functionality, such as, for example, about 2.5 centimeters, about 2 centimeters, or about 1 centimeter. Examples of elastomeric films suitable for use as either an elastomeric film web core layer 5a or as the elastomeric film ribbon web 7 are disclosed in U.S. Patent Application Publications 2008/0076315, 2008/0095978, and 2009/0197041, each of which is assigned to Kimberly-Clark Worldwide, Inc. and each of which is incorporated by reference herein to the extent not inconsistent herewith. In particular embodiments, it may be desirable to produce an elastomeric film "off line" for one or both of the core layer 5a and the ribbon layer 7, such that the film can be collected, such as via a roll or spool, and delivered to and unwound into the manufacturing process for the personal care article in question. Examples of suitable films are disclosed in U.S. Patent Application Publications 2008/0076315, 2008/0095978, and 2009/0197041. It has been discovered that certain films, such as films based upon some of those disclosed in the preceding publications, can be wound into roll form by taking measures to limit the surface tack of the film. For example, in certain embodiments, a film is created which includes a central layer substantially devoid of inorganic matter, sandwiched by one or two film skin layers, one or both of which include inorganic matter. In a particular example, a film layer suitable for use in conjunction with the present invention includes a central layer comprised of 100% VISTAMAXX™ propylene polymer from ExxonMobil Chemical Co. of Houston, Tex., sandwiched on one or both of its faces by a skin layer(s), the skin layer being comprised of 30% VISTAMAXX™ propylene polymer and 70% inorganic material, such as calcium carbonate ($CaCO_3$). Such an exemplary construction allows the film layer to be collected into roll form, and subsequently unwound into a laminate manufacturing process without undesirable binding of the layers on the roll, and still thermally fused to other layers of the laminate, as shall be described below.

The method further includes sandwiching the core layer of elastomeric material 5 between the first nonwoven web 1 and the second nonwoven web 2, and also sandwiching the elastomeric film ribbon web 7 between the first nonwoven web 1 and the second nonwoven web 2. In certain embodiments, such as that shown in FIG. 1, the core layer 5 is positioned in a side-by-side relationship with the ribbon web 7, such that the two are not superposed over one another. In other embodiments, such as that shown in FIGS. 2-4, the core layer 5 is superposed over the ribbon web 7, such that the ribbon web 7 is partially or entirely overlapped by the core layer 5. For example, in an embodiment where the core layer 5 is an elastomeric film web core layer 5a, the elastomeric film web core layer 5a may not be superposed over the elastomeric film ribbon layer 7 as representatively illustrated in FIG. 1, or, alternatively, the elastomeric film web core layer 5a may be superposed over the elastomeric film ribbon layer 7 as representatively illustrated in FIGS. 2-4. In one embodiment, the elastomeric ribbon web 7 comprises a folded-over, integrally formed portion of the elastomeric film web core layer 5a (not shown). The basis weights of the film web core layer 5a and the film ribbon web 7 can vary depending on the functional elastic properties desired in the personal care article. In one example, the basis weights of the film web core layer 5a and the film ribbon web 7 are the same. In another example, they differ by at least 10%, and preferably by at least 20%.

The method in particular embodiments further includes bonding the core layer of elastomeric material 5 to at least one of the first nonwoven web 1 and the second nonwoven web 2. In particular embodiments, such as that representatively illustrated in FIGS. 1, 2, and 4, the process includes bonding the core layer 5a to both the first nonwoven web 1 and the second nonwoven web, such as in embodiments in which the core layer is an elastomeric film core layer 5a. In other embodiments, the core layer 5a is "pre-bonded" to one of the nonwoven webs, such as the first nonwoven web 1, in a precursor procedure. If the material is supplied in such manner (that is, supplied to the personal care article manufacturing process in a "half laminate" roll form in which one side of the film core layer has already been at least provisionally mated with a nonwoven web, but wherein the opposite side of the film core layer has not yet been mated with a nonwoven web, and remains exposed), then the process can include bonding the core layer 5a to just one of the first and second nonwoven webs 1, 2.

The method in particular embodiments further includes bonding the elastomeric film ribbon web 7 to the first and second nonwoven webs 1, 2 by fusing the elastomeric film ribbon web to the first and second nonwoven webs, such as via the use of heat, pressure, and/or ultrasonic energy. In one example, a heated, patterned embossing roll is used to perform the fusing. Desirably, the nature of the film allows it to be bonded to the nonwoven webs without the use of adhesive, but merely via the introduction of energy such as heat, pressure, or ultrasonic energy. Accordingly, in particular embodiments, the elastomeric film ribbon web 7 is bonded to the first and second nonwoven webs 1, 2 solely by fusing, without the use of adhesive Examples of such techniques are taught in U.S. Patent Application Publications 2008/0076315, 2008/0095978, and US 2009/0197041, referenced above. In particular embodiments, the film ribbon web 7 can be directly fused to one or both of the first and second nonwoven webs 1/2, such as representatively illustrated in FIG. 1. Alternatively, the film ribbon web 7 can be directly fused to one of the nonwoven webs, and indirectly fused to the other nonwoven web by way of being directly and intermediately fused to the core layer 5 or to another layer, such as representatively illustrated in the embodiments of FIGS. 2-4.

If the core layer of elastomeric material 5 is an elastomeric film web core layer 5a, in particular embodiments, bonding the core layer of elastomeric material to at least one of the first and second nonwoven webs 1, 2 includes fusing the elastomeric film web core layer to at least one of the first and second nonwoven webs 1, 2. In one example, a heated, patterned embossing roll is used to perform the fusing. In particular embodiments, the elastomeric film web core layer 5a is bonded to at least one of the first and second nonwoven webs solely by fusing, without the use of adhesive. Examples of such techniques are taught in U.S. Patent Application Publications 2008/0076315, 2008/0095978, and US 2009/0197041, referenced above. For example, in particular embodiments, the method includes fusing the elastomeric film web core layer 5a to one or both of the first and second nonwoven webs 1,2 using heat, pressure, and/or ultrasonic energy. In one desirable embodiment, both the elastomeric film web core layer 5a and the elastomeric film ribbon web 7 are fused, either directly or indirectly, to the first nonwoven web 1 and the second nonwoven web 2 without the use of adhesive, such as via the use of heat, pressure, and/or ultrasonic energy. Using such a technique can in particular embodiments result in certain benefits. First, eliminating the conventional use of adhesive to bond the layers within the elastomeric laminate reduces material cost. Second, eliminating the conventional use of adhesive reduces the cost, maintenance, and delay associated with adhesive application equipment. Finally, if the material used to form the elastomeric film web core layer 5a is the same as, or is chemically compatible with, the material used to form the nonwoven webs materials 1,2, waste or scrap from the entire resulting laminate can be recycled and reused to make new nonwoven webs, new elastomeric film webs, or other materials. In a particular example, the elastomeric film web core layer 5 and the elastomeric film ribbon web 7 are comprised primarily (but not necessarily entirely) of polypropylene, and the nonwoven webs 1, 2 are also comprised primarily (but not necessarily entirely) of polypropylene. Desirably (but optionally), both the elastomeric film web core layer 5a and the elastomeric film ribbon web 7 are fused, either directly or indirectly, to the first nonwoven web 1 and the second nonwoven web 2 without the use of adhesive in a single operation.

In another aspect, the present invention pertains to a method 30 of manufacturing a plurality of disposable absorbent garments 32; examples of the method are representatively illustrated in FIGS. 5-8. The method 30 builds on the method 10 of forming an elastomeric laminate having targeted elastic properties described above. In particular embodiments, the method 30 comprises providing a first nonwoven web 1, such as an outer cover web 1a, traveling in a machine direction 20. The outer cover web 1a in particular embodiments defines a front edge 26 and a back edge 28, both of which extend in the machine direction 20.

The method 30 in particular embodiments further includes providing at least one second nonwoven web 2, such as a pair of nonwoven liner webs 2a, 2b. The method 30 further includes providing at least one core layer of elastomeric material 5 under tension, such as a first core layer 5a and second core layer 5b. Each core layer 5a, 5b has a cross-direction width at least 75% that of the width of at least one of the first nonwoven web 1a and the corresponding second nonwoven webs 2a, 2b. In the examples of FIGS. 5-8, the core layers 5a, 5b each have a width that approaches 100% that of the width of each of the respective second nonwoven liner webs 2a, 2b. The method further includes sandwiching each core layer of elastomeric material 5a, 5b between the outer cover web 1a and the respective nonwoven liner web or webs 2a, 2b. The method further includes bonding the core layer of elastomeric material 5 to the first nonwoven web 1, to the second nonwoven web(s) 2, or to both, such as via fusing as described above. In particular embodiments, the outer cover web 1a may be provided by two separate outer cover webs, as in the example of FIG. 7. Such an embodiment therefore includes a pair of first nonwoven webs 1b, 1c, a pair of second nonwoven webs 2a, 2b, and a pair of core layers 5a, 5b.

Figure 6:
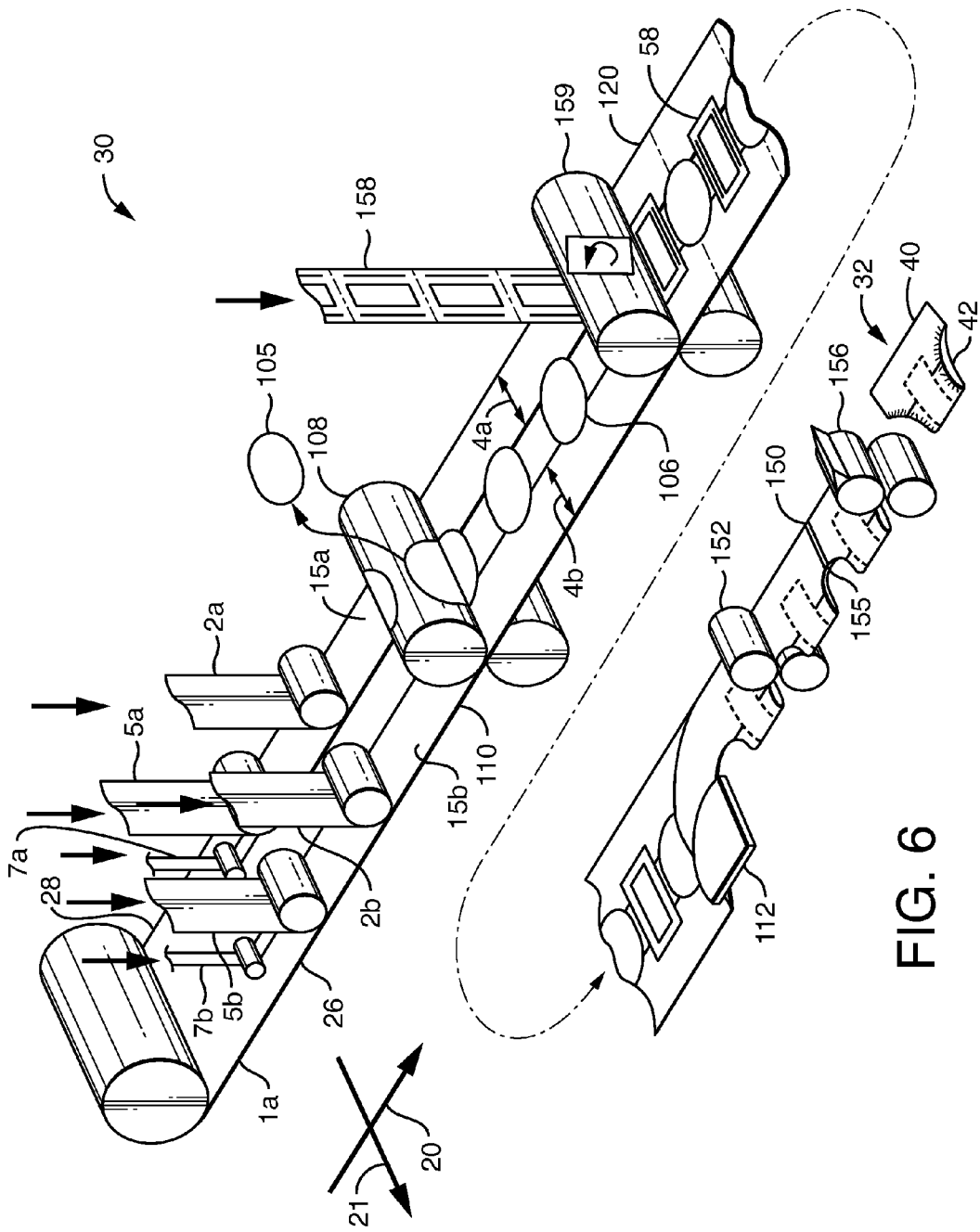
FIG. 6 representatively illustrates a perspective view of an alternative embodiment of a garment manufacturing process incorporating principles of the present invention.
Figure 7:
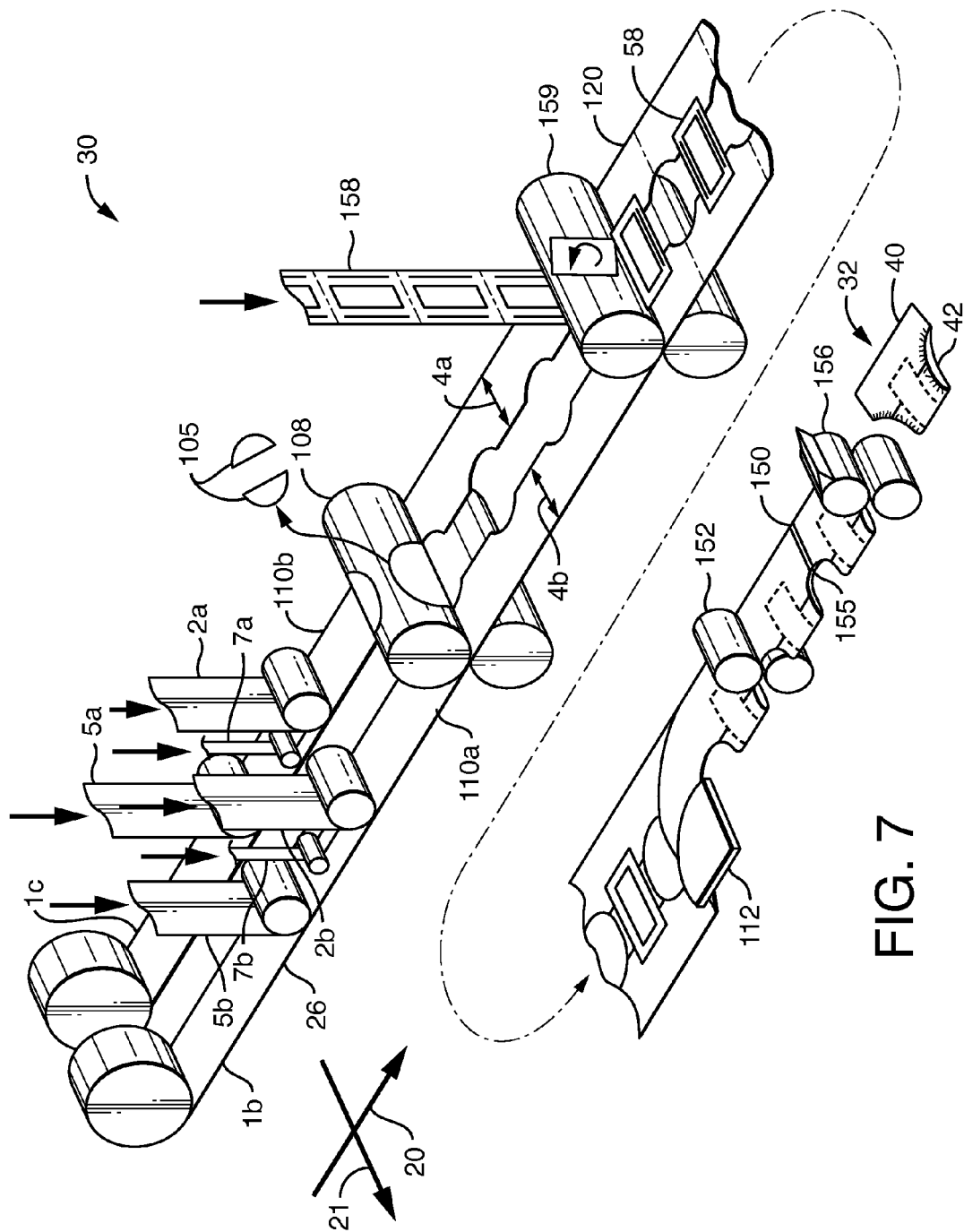
FIG. 7 representatively illustrates a perspective view of another alternative embodiment of a garment manufacturing process incorporating principles of the present invention.
Figure 8:
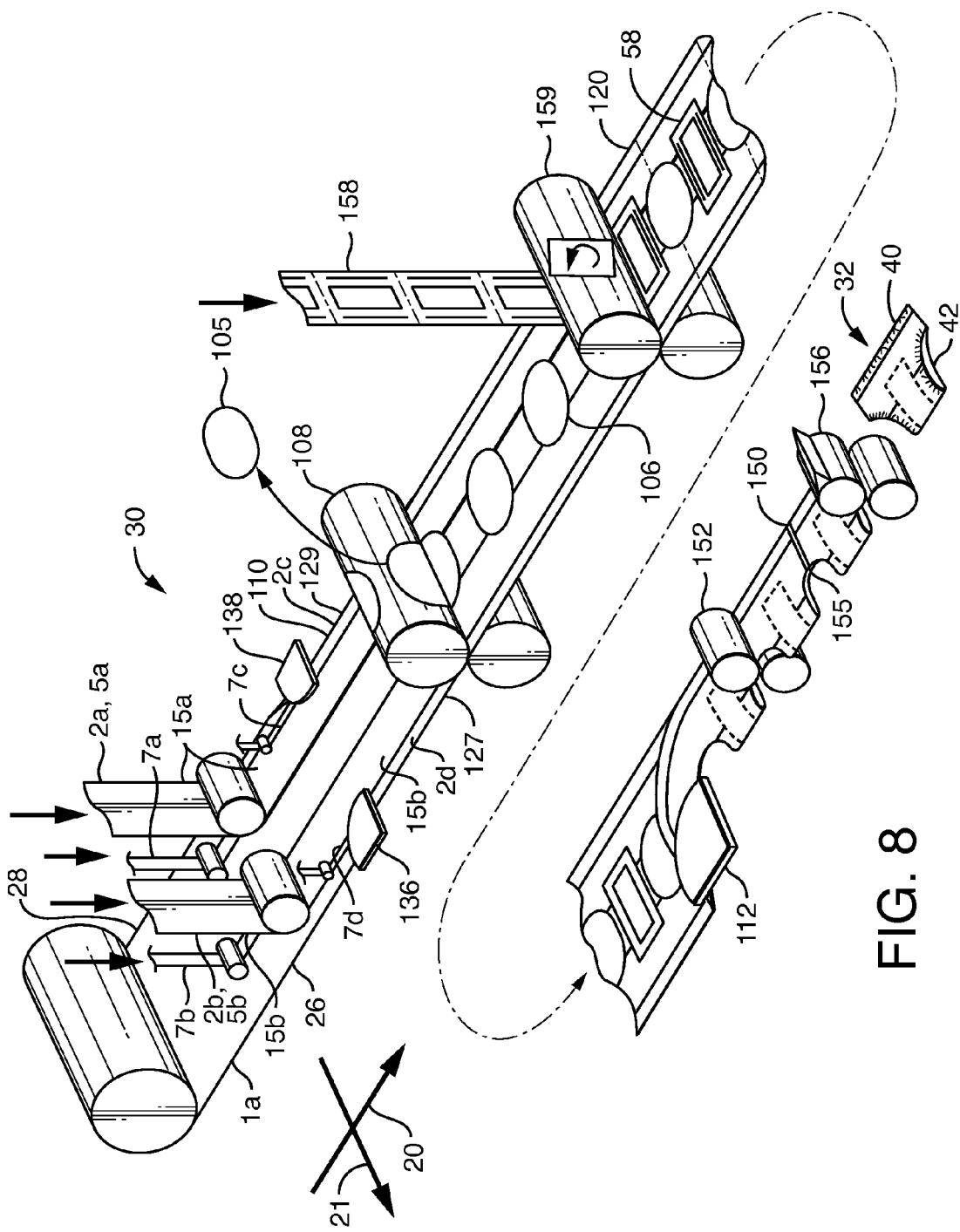
FIG. 8 representatively illustrates a perspective view of yet another alternative embodiment of a garment manufacturing process incorporating principles of the present invention.

As described above, in particular embodiments, such as that representatively illustrated in FIGS. 6 and 7, the process includes bonding (for example, by fusing) the core layer 5a to both the first nonwoven web 1a/1b and the second nonwoven web 2a/2b, such as in embodiments in which the core layer is an elastomeric film core layer 5a/5b. In these embodiments, each core layer 5 and each nonwoven web 2 is separately provided, and they are laminated together during the continuous machine manufacture of the garments. For example, as representatively illustrated in FIGS. 6 and 7, in one embodiment the method includes providing a roll supply of elastomeric film web core layer 5a/5b and providing a separate roll supply of nonwoven webs 2a, 2b. In other embodiments, the core layer 5a/5b is "pre-bonded" to one of the nonwoven webs, such as a second nonwoven web 2, in a precursor procedure. If the material is supplied in such manner (that is, supplied to the personal care article manufacturing process in a "half laminate" roll form in which one side of the film core layer has already been mated with a nonwoven web, but wherein the opposite side of the film core layer has not yet been mated with a nonwoven web, and remains exposed), then the process includes bonding the core layer 5a to the first nonwoven web 1, the second nonwoven web 2, or both. For example, as representatively illustrated in FIGS. 5 and 8, the method can include providing a single roll supply of elastomeric film laminate 15 (shown in the example as two separate supplies of film laminate 15a and 15b), wherein the laminate 15 on the roll supply(ies) comprises at least two layers, one layer being an elastomeric film web core layer 5a/5b and the other layer being a nonwoven layer 2a/2b, to provide a premade, "one-sided" elastomeric laminate 15a/15b. Note that in FIGS. 15 and 18, individual layers of the elastomeric film laminate 15 are not depicted, but instead the laminate is depicted as a single, "pre-made" laminate substrate.

In the embodiments of FIGS. 5-8, the outer cover web 1a (and in the case of FIG. 7, web 1b), the nonwoven webs 2a, 2b, and the core layers of elastomeric material 5a, 5b collectively define a composite garment web 110. (Note that in the example of FIG. 7, the composite garment web 110 is defined by two composite garment web portions 110a and 110b.) The method 30 in particular embodiments further includes providing a supply 158 of individual absorbent assemblies 58, superposing individual absorbent assemblies 58 over the composite garment web 110, and attaching the individual absorbent assemblies 58 to the composite garment web 110. In certain embodiments, such as those representatively illustrated in FIGS. 5-8, the absorbent assemblies may be manufactured in one orientation, and then cut and rotated 90 degrees (such as at cut-and-rotate station 159) before attachment to the composite garment web 110. The method can in particular embodiments further include removing portions 105 of the composite garment web 110 (such as at cutting station 108) to define a series of spaced apart holes 106, thereby defining in the composite garment web 110 an interconnected series 120 of disposable absorbent garments 32. Such portions 105 can be removed from the outer cover web 1a before the nonwoven webs 2a, 2b and the core layers 5a, 5b are attached to the outer cover web 1a (not shown), or can be removed from the outer cover web 1a after the nonwoven webs 2a, 2b and the core layer 5a, 5b are attached to the outer cover web 1a (as representatively illustrated in FIGS. 5-8). Furthermore, such portions 105 can be removed from the composite garment web 110 before the individual absorbent assemblies 58 are attached to the composite garment web 110 (as representatively illustrated in FIGS. 5-8), or can be removed from the composite garment web 110 after the individual absorbent assemblies 58 are attached to the composite garment web (not shown).

The method 30 can further include folding the composite garment web 110, such as at a garment folding station 112, along a transversely centered longitudinal fold line that extends in the machine direction 20, such that the front edge 26 is brought into close proximity with the back edge 28. In particular embodiments, the method further comprises creating a series of side seam bonds 150 (such as at seaming station 152) spaced apart in the machine direction 20. The method additionally comprises cutting the composite garment web 110 at a series of cut locations 155 (such as at cutting station 156) spaced apart in the machine direction 20 to create the plurality of disposable absorbent garments.

The method 30 further includes providing at least one elastomeric film ribbon web 7 under tension, sandwiching the elastomeric film ribbon web 7 between two nonwoven web layers, such as the first nonwoven web 1a and the second nonwoven web or webs 2a, 2b, and bonding via fusing, directly or indirectly (as explained above), the elastomeric film ribbon web 7 to the first and second nonwoven webs 1, 2, preferably without the use of adhesive. When donned, the personal care garment defines a waist opening 40 and two leg openings 42. In particular embodiments, the elastomeric film ribbon web 7 is positioned adjacent the waist opening 40, the front edge of a leg opening 42, and/or the back edge of a leg opening 42. For example, in particular embodiments, the method 30 includes attaching a continuous back leg elastic ribbon web 7a to the outer cover web 1a/1b or to one of the nonwoven liner webs 2a, 2b. The back leg elastic ribbon web 7a extends or travels predominantly in the machine direction 20. In particular embodiments, as representatively illustrated in FIGS. 5-8, the method further comprises partially or entirely overlapping the back leg elastic ribbon web 7a with the core layer 5. For example, the method may comprise sandwiching at least a portion of the continuous back leg elastic ribbon web 7a between the core layer 5 and the outer cover web 1 (FIGS. 5, 6, and 8), or between the core layer 5 and the nonwoven web or webs 2 (FIG. 7). Similarly, in particular embodiments, the method 30 also includes attaching a continuous front leg elastic ribbon web 7b to the outer cover web 1a/1b or to one of the nonwoven liner webs 2a, 2b. The front leg elastic member 7b extends or travels predominantly in the machine direction 20. In particular embodiments, as representatively illustrated in FIGS. 5-8, the method further comprises partially or entirely overlapping the front leg elastic ribbon web 7b with the core layer 5. For example, the method may comprise sandwiching at least a portion of the continuous front leg elastic ribbon web 7b between the core layer 5 and the outer cover web 1 (FIGS. 5, 6, and 8), or between the core layer 5 and the nonwoven web or webs 2 (FIG. 7).

In particular embodiments, the method 30 also can include sandwiching continuous waist elastic ribbon webs 7c and 7d between the outer cover web(s) 1a/1b and the nonwoven liner webs 2a, 2b. In one embodiment, a waist elastic ribbon web 7 is sandwiched in a straight line, and a leg elastic ribbon web is sandwich in an oscillating curved line (see, for example, FIG. 4). In one variant, such as that representatively illustrated in FIG. 8, the method can include folding the edge of one or both of first nonwoven web 1a or the second nonwoven web or webs 2a, 2b. For example, in one embodiment, the method includes folding the front edge 26 of the outer cover web 1a, such as at a front waistband folding station 136, to create a front waist edge fold 127 and to sandwich the ribbon web 7*d* within the fold. In such an embodiment, the second nonwoven web 2*d* comprises an integrally formed, folded-over portion of the first nonwoven web 1*a*. The method may instead or additionally include folding the edge 128 of the outer cover web 1*a*, such as at a back waistband folding station 138, to create a back waist edge fold 129 and to sandwich the ribbon web 7*c* within the fold. In such an embodiment, the second nonwoven web 2*c* comprises an integrally formed, folded-over portion of the first nonwoven web 1*a*.

In certain embodiments, the method 30 further comprises at least partially deactivating the elastomeric properties of one or more of the core layers 5, of one or more of the ribbon webs 7, or both, using heat, ultrasonics, pressure, or other techniques. In particular embodiments, portions of both a core layer 5 and a ribbon web 7 are deactivated in a single process step, such as via a single rotary deactivating or "deadening" device. Examples of techniques to deaden or deactivate elastic properties in various elastomeric laminates are disclosed in U.S. Pat. No. 5,660,657 issued May 5, 1998 to Raj ala et al. and assigned to Kimberly-Clark Worldwide, Inc., and also disclosed in U.S. application Ser. No. 12/605,092.

In particular embodiments, various components, such as the outer cover web 1*a*, the liner webs 2*a*, 2*b*, the core webs 5*a*, 5*b*, or the ribbon webs 7*a*, 7*b*, 7*c*, 7*d* can be printed or pigmented to include graphics, text, color, or other images. Such printing can occur during assembly of the garment in conjunction with the presently disclosed method, or can occur prior to such assembly in an off-line, "pre-preprinting" or pigmenting step.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of forming an elastomeric laminate having targeted elastic properties for use in personal care articles, the method defining a machine direction and a cross-machine direction, the method comprising:
   providing first and second nonwoven webs, each defining a cross-direction width;
   providing a core layer of elastomeric material under tension, said core layer having a cross-direction width at least 75% that of the width of at least one of the first and second nonwoven webs;
   sandwiching said core layer of elastomeric material between said first and second nonwoven webs;
   bonding the core layer of elastomeric material to at least one of the first and second nonwoven webs;
   providing an elastomeric film ribbon web under tension;
   sandwiching said elastomeric film ribbon web between said first and second nonwoven webs; and
   bonding the elastomeric film ribbon web to the first and second nonwoven webs by fusing the elastomeric film ribbon web to the first and second nonwoven webs.

2. The method of claim 1, wherein the elastomeric film ribbon web is bonded to the first and second nonwoven webs solely by fusing, without the use of adhesive.

3. The method of claim 1, wherein the core layer of elastomeric material width is at least 90% that of the width of at least one of the first and second nonwoven webs.

4. The method of claim 1, wherein the core layer of elastomeric material is an elastomeric film web core layer.

5. The method of claim 4, wherein the elastomeric film web core layer width is at least 90% that of the width of at least one of the first and second nonwoven webs.

6. The method of claim 5, wherein the elastomeric film web core layer is superposed over the elastomeric film ribbon web.

7. The method of claim 4, wherein bonding the core layer of elastomeric material to at least one of the first and second nonwoven webs comprises fusing the elastomeric film web core layer to said at least one of the first and second nonwoven webs.

8. The method of claim 7, wherein the elastomeric film web core layer is bonded to said at least one of the first and second nonwoven webs solely by fusing, without the use of adhesive.

9. The method of claim 8, wherein the elastomeric film web core layer is bonded to both of the first and second nonwoven webs solely by fusing, without the use of adhesive.

10. A method of manufacturing a personal care garment, the garment comprising an elastomeric laminate having targeted elastic properties, the method defining a machine direction and a cross-machine direction, the method comprising:
    providing first and second nonwoven webs, each defining a cross-direction width;
    providing a core layer of elastomeric material under tension, said core layer having a cross-direction width at least 75% that of the width of at least one of the first and second nonwoven webs;
    sandwiching said core layer of elastomeric material between said first and second nonwoven webs;
    bonding the core layer of elastomeric material to at least one of the first and second nonwoven webs;
    providing an elastomeric film ribbon web under tension;
    sandwiching said elastomeric film ribbon web between said first and second nonwoven webs; and
    bonding the elastomeric film ribbon web to the first and second nonwoven webs by fusing the elastomeric film ribbon web to the first and second nonwoven webs,
    wherein when donned, the personal care garment defines a waist opening and two leg openings, and wherein the elastomeric film ribbon web is positioned adjacent at least one of the waist opening and the two leg openings.

11. The method of claim 10, wherein the elastomeric film ribbon web is bonded to the first and second nonwoven webs solely by fusing, without the use of adhesive.

12. The method of claim 10, wherein the core layer of elastomeric material width is at least 90% that of the width of at least one of the first and second nonwoven webs.

13. The method of claim 10, wherein the core layer of elastomeric material is an elastomeric film web core layer.

14. The method of claim 13, wherein the elastomeric film web core layer width is at least 90% that of the width of at least one of the first and second nonwoven webs.

15. The method of claim 14, wherein the elastomeric film web core layer is superposed over the elastomeric film ribbon web.

16. The method of claim 13, wherein bonding the core layer of elastomeric material to at least one of the first and second nonwoven webs comprises fusing the elastomeric film web core layer to said at least one of the first and second nonwoven webs.

17. The method of claim 16, wherein the elastomeric film web core layer is bonded to said at least one of the first and second nonwoven webs solely by fusing, without the use of adhesive.

18. The method of claim 17, wherein the elastomeric film web core layer is bonded to both of the first and second nonwoven webs solely by fusing, without the use of adhesive.

* * * * *